(12) United States Patent
Gurevich et al.

(10) Patent No.: US 11,197,692 B2
(45) Date of Patent: Dec. 14, 2021

(54) EXTERNAL FIXATION STABILIZERS, SYSTEMS, KITS, AND METHODS

(71) Applicant: GLW, Inc., Waxhaw, NC (US)

(72) Inventors: Vadim Gurevich, Toms River, NJ (US); Axel Cremer, Fahrenkrug (DE)

(73) Assignee: GLW, Inc., Englewood Cliffs, NJ (US)

( * ) Notice: Subject to any disclaimer, the term of this patent is extended or adjusted under 35 U.S.C. 154(b) by 245 days.

(21) Appl. No.: 16/661,246

(22) Filed: Oct. 23, 2019

(65) Prior Publication Data

US 2020/0129207 A1 Apr. 30, 2020

Related U.S. Application Data

(60) Provisional application No. 62/749,936, filed on Oct. 24, 2018.

(51) Int. Cl.
*A61B 17/64* (2006.01)
*A61B 17/86* (2006.01)

(52) U.S. Cl.
CPC .... *A61B 17/6441* (2013.01); *A61B 2017/867* (2013.01)

(58) Field of Classification Search
CPC ... A61B 17/6441; A61B 17/62; A61B 17/645; A61B 17/867
(Continued)

(56) References Cited

U.S. PATENT DOCUMENTS 4,600,000 A 7/1986 Edwards
4,784,125 A 11/1988 Monticelli et al.
(Continued)

FOREIGN PATENT DOCUMENTS

EP 2937049 10/2015
EP 3245966 11/2017
(Continued)

OTHER PUBLICATIONS

International Searching Authority. International Search Report and Written Opinion, dated Feb. 7, 2020, pp. 1-11.
(Continued)

*Primary Examiner* — Eduardo C Robert
*Assistant Examiner* — David C Comstock
(74) *Attorney, Agent, or Firm* — MacMillan, Sobanski & Todd, LLC (57) ABSTRACT

The disclosure relates to orthopedic medical devices for fixating, immobilizing, and manipulating bones, components of these medical devices, and methods. Specific examples relate to external fixation stabilizers and assemblies suitable for spacing a footplate from the ground. An external fixation stabilizer assembly includes a base member that defines an upper cavity and a lower cavity, a spacer defining a passageway, a connector member partially disposed in the lower cavity and extending into the upper cavity and through the spacer passageway, and a footing member attached to the lower surface of the base member. The spacer is movable between a first orientation on the connector in which a portion of the spacer extends into the upper cavity and a second orientation in which no portion of the spacer is disposed in the upper cavity. The disclosure also relates to external fixation systems, external fixation kits, and various related methods.

20 Claims, 9 Drawing Sheets

(58) Field of Classification Search
USPC .................. 606/54, 55, 56, 59; 623/53, 55
See application file for complete search history.

(56) References Cited

U.S. PATENT DOCUMENTS

| | | | |
|---|---|---|---|
| 5,968,043 A | 10/1999 | Ross, Jr. et al. | |
| 8,323,282 B2 | 12/2012 | Taylor | |
| 8,945,128 B2 | 2/2015 | Singh et al. | |
| 9,757,153 B2* | 9/2017 | Jay | A61B 17/62 |
| 9,808,288 B2 | 11/2017 | Wong et al. | |
| 9,827,011 B2 | 11/2017 | Cresina et al. | |
| 9,839,445 B2 | 12/2017 | Singh et al. | |
| 9,839,568 B2 | 12/2017 | Butler | |
| 10,743,917 B2* | 8/2020 | Ross | A61B 17/6425 |
| 2005/0038525 A1* | 2/2005 | Doddroe | A61F 2/66 623/55 |
| 2007/0203585 A1* | 8/2007 | Wilson | A61F 2/66 623/55 |
| 2012/0232554 A1 | 9/2012 | Shaevitz et al. | |
| 2012/0277746 A1 | 11/2012 | Lizee | |
| 2014/0278325 A1 | 9/2014 | Burgherr et al. | |
| 2017/0042580 A1 | 2/2017 | Mannanal et al. | |
| 2017/0291270 A1 | 10/2017 | Brown et al. | |
| 2018/0028231 A1 | 2/2018 | Singh et al. | |
| 2019/0119064 A1* | 4/2019 | Wong | A61B 17/62 |
| 2020/0000492 A1* | 1/2020 | Samchukov | A61B 17/62 |

FOREIGN PATENT DOCUMENTS

| | | |
|---|---|---|
| IL | 258396 | 5/2018 |
| WO | WO2017083033 | 5/2017 |

OTHER PUBLICATIONS

Anonymous, "gme adjustable feet / machine feet / adjustable feet / ALS2 M10×100 loadable up to 300 kg," retrieved from Internet Mar. 11, 2020, pp. 1-4. <URL: https://www.amazon.de/Stellf%C3%BC%C3%9Fe-Maschinenf%C3%BC%C3%9Fe-Verstellf%C3%BCsse-M10x100-belastbar/dp/B074G339W5>.

* cited by examiner

EXTERNAL FIXATION STABILIZERS, SYSTEMS, KITS, AND METHODS

CROSS-REFERENCE TO RELATED APPLICATIONS

This application claims priority to U.S. provisional application No. 62/749,936, filed on Oct. 24, 2018. This related application is incorporated by reference into this disclosure in its entirety.

FIELD

The disclosure relates to the field of medical devices. More particularly, the disclosure relates to orthopedic medical devices for fixating, immobilizing, and manipulating bones, and components of these medical devices. Specific examples relate to external fixation stabilizers suitable for spacing a footplate from the ground. The disclosure also relates to external fixation systems, external fixation kits, and various related methods.

BACKGROUND

There is a need for improved external fixation stabilizers, external fixation stabilizer assemblies, external fixation systems, external fixation kits, and various related methods.

BRIEF SUMMARY OF SELECTED EXAMPLES

Various external fixation stabilizers are described and illustrated herein.

An example external fixation stabilizer comprises a non-metallic base member having an upper surface and a lower surface; a connector member extending from the upper surface of the base member; and a footing member attached to the lower surface of the base member and comprising a non-metallic material.

Another example external fixation stabilizer comprises a non-metallic base member having an upper surface and a lower surface, the upper surface defining a cavity; a connector member partially disposed in the cavity of the base member and extending away from the base member; and a footing member attached to the lower surface of the base member and comprising a non-metallic material.

Another example external fixation stabilizer comprises a non-metallic base member having an upper surface, a lower surface, an outer circumferential wall, an upper inner circumferential wall, a lower inner circumferential wall, and a separating wall defining an opening disposed between the upper inner circumferential wall and the lower inner circumferential wall, the upper inner circumferential wall and the separating wall cooperatively defining an upper cavity that extends from the upper surface to the separating wall, the lower inner circumferential wall and the separating wall cooperatively defining a lower cavity that extends from the lower surface to the separating wall; a connector member partially disposed in the lower cavity and extending through the opening and into the upper cavity; and a footing member attached to the lower surface of the base member and comprising a non-metallic material.

Various external fixation stabilizer assemblies are described.

An example external fixation stabilizer assembly comprises a non-metallic base member having an upper surface, a lower surface, an outer circumferential wall, an upper inner circumferential wall, a lower inner circumferential wall, and a separating wall defining an opening disposed between the upper inner circumferential wall and the lower inner circumferential wall, the upper inner circumferential wall and the separating wall cooperatively defining an upper cavity that extends from the upper surface to the separating wall, the lower inner circumferential wall and the separating wall cooperatively defining a lower cavity that extends from the lower surface to the separating wall; a spacer having a base portion defining a first terminal surface, an extension portion defining a second terminal surface, an outer wall defining a shoulder comprising an interface between the base portion and the extension portion, and an inner circumferential wall defining a passageway extending from the first terminal surface to the second terminal surface; a connector member partially disposed in the lower cavity and having a shaft extending into the upper cavity and through the passageway of the spacer; and a footing member attached to the lower surface of the base member and comprising a non-metallic material.

Various example external fixation systems are described.

An example external fixation system comprises a plate having a plate upper surface and a plate lower surface and defining a first passageway extending from the plate lower surface to the plate upper surface and a second passageway extending from the plate lower surface to the plate upper surface; a first external fixation stabilizer comprising a first non-metallic base member having a first upper surface and a first lower surface, a first connector member extending from the first upper surface of the first base member, and a first footing member attached to the first lower surface of the first base member and comprising a non-metallic material; and a second external fixation stabilizer comprising a second non-metallic base member having a second upper surface and a second lower surface, a second connector member extending from the second upper surface of the second base member, and a second footing member attached to the second lower surface of the second base member and comprising a non-metallic material. The first connector member is disposed through the first passageway and the second connector member is disposed through the second passageway.

Various example external fixation kits are described.

An example external fixation kit comprises a first external fixation stabilizer comprising a non-metallic base member having an upper surface and a lower surface; a connector member extending from the upper surface of the base member; and a footing member attached to the lower surface of the base member and comprising a non-metallic material; a second external fixation stabilizer comprising a non-metallic base member having an upper surface and a lower surface, the upper surface defining a cavity; a connector member partially disposed in the cavity of the base member and extending away from the base member; and a footing member attached to the lower surface of the base member and comprising a non-metallic material; a spacer having a base portion defining a first terminal surface, an extension portion defining a second terminal surface, an outer wall defining a shoulder comprising an interface between the base portion and the extension portion, and an inner circumferential wall defining a passageway extending from the first terminal surface to the second terminal surface; and a packaging substrate.

Another example external fixation kit comprises a first external fixation stabilizer comprising a non-metallic base member having an upper surface and a lower surface; a connector member extending from the upper surface of the base member; and a footing member attached to the lower surface of the base member and comprising a non-metallic material; a second external fixation stabilizer comprising a non-metallic base member having an upper surface and a lower surface, the upper surface defining a cavity; a connector member partially disposed in the cavity of the base member and extending away from the base member; and a footing member attached to the lower surface of the base member and comprising a non-metallic material; a first spacer having a base portion defining a first terminal surface, an extension portion defining a second terminal surface, an outer wall defining a shoulder comprising an interface between the base portion and the extension portion, and an inner circumferential wall defining a passageway extending from the first terminal surface to the second terminal surface; a second spacer having a base portion defining a first terminal surface, an extension portion defining a second terminal surface, an outer wall defining a shoulder comprising an interface between the base portion and the extension portion, and an inner circumferential wall defining a passageway extending from the first terminal surface to the second terminal surface; a plate having a plate upper surface and a plate lower surface and defining a first passageway extending from the plate lower surface to the plate upper surface and a second passageway extending from the plate lower surface to the plate upper surface; and a packaging substrate Various example methods are also described.

An example method comprises attaching a first external fixation stabilizer to an external fixation plate; and attaching a second external fixation stabilizer to the external fixation plate.

Another example method comprises attaching a spacer to a first external fixation stabilizer; attaching the first external fixation stabilizer to an external fixation plate; and attaching a second external fixation stabilizer to the external fixation plate.

Additional understanding of the claimed devices and methods can be obtained by reviewing the detailed description of selected examples, below, with reference to the appended drawings.

DETAILED DESCRIPTION OF SELECTED EXAMPLES

The following detailed description and the appended drawings describe and illustrate various example medical devices, components of medical devices, systems, kits, and methods individually selected by the inventors for the purpose of enabling one skilled in the art to make and use examples of the inventive medical devices, components, systems, and kits, and to perform examples of the inventive methods. The examples do not limit the scope of the claims in any manner.

FIGS. 1, 2, 3, and 4 illustrate a first example external fixation stabilizer 100. External fixation stabilizer 100 includes a base member 110, a connector member 112 extending away from the base member 110, and a footing member 114 secured to the base member 110. In this example, external fixation stabilizer 100 and its base member 110, connector member 112, and footing member 114 share common lengthwise axis 116.

Figure 4:
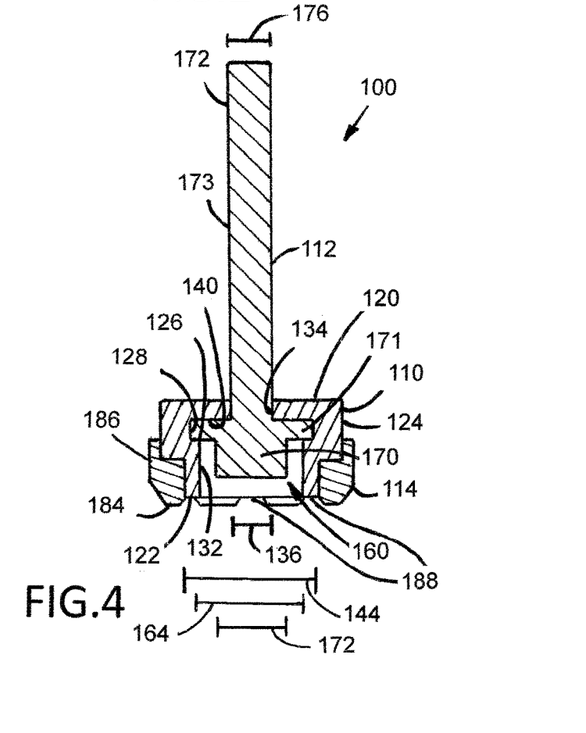
FIG. 4 is a sectional view of the first example external fixation stabilizer, taken along line 4-4 in FIG. 2.

As best illustrated in FIG. 4, base member 110 has an upper surface 120, a lower surface 122, an outer circumferential wall 124, and a circumferential shoulder 126 that lies on a plane that is perpendicular to common lengthwise axis 116. An upper inner circumferential wall 128 and the circumferential shoulder 126 cooperatively define an upper cavity 140. Similarly, a lower inner circumferential wall 132 defines a lower cavity 160 that extends from the lower surface 122, into the base member 110 to the circumferential shoulder 126. Upper surface 120 defines an opening 134 having an opening inner diameter 136. As best illustrated in FIG. 4, the connector member 112 extends through the opening 134 such that a portion of the connector member 112 is disposed in the lower cavity 160, a portion of the connector member 112 is disposed in the upper cavity 140, and a portion of the connector member 112 is disposed in the opening 134 of the upper surface 120.

As best illustrated in FIG. 4, in this example, the upper inner circumferential wall 128 is a continuous annular surface free of ribs or other structural interruptions to the surface. In this example, this configuration is considered advantageous at least because it provides a desirable interface between the connecting member 112 and the base member 110. It is noted, though, that other configurations can be included in an external fixation stabilizer according to a particular embodiment.

Figure 1:
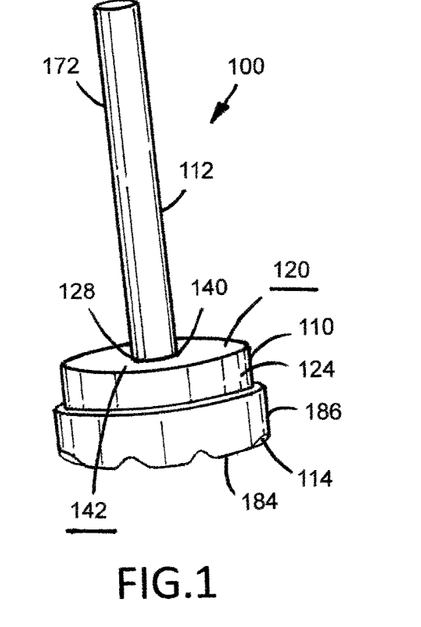
FIG. 1 is a perspective view of a first example external fixation stabilizer.
Figure 2:
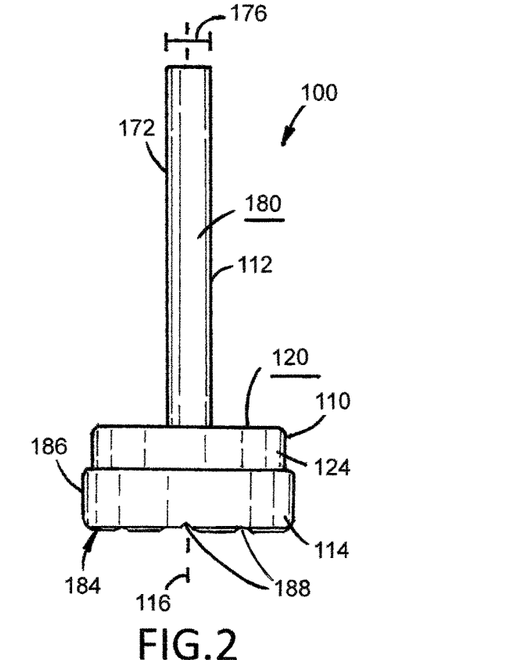
FIG. 2 is a side view of the first external fixation stabilizer.
Figure 3:
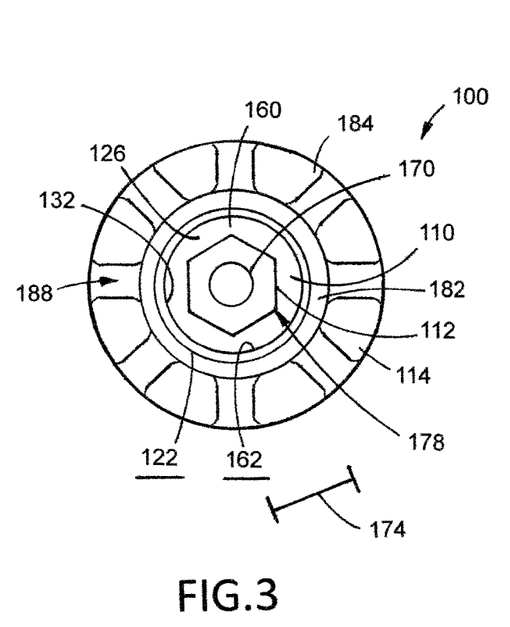
FIG. 3 is a bottom view of the first example external fixation stabilizer.

Also as best illustrated in FIGS. 3 and 4, in this example, the lower inner circumferential wall 132 is a continuous annular surface free of corrugations or other structural interruptions to the surface. In this example, this configuration is considered advantageous at least because it facilitates interaction with the connector member 112, as described in detail below. It is noted, though, that other configurations can be included in an external fixation stabilizer according to a particular embodiment.

The upper inner circumferential wall 128 defines an inner diameter 144 for the upper cavity 140 and the lower circumferential wall 132 defines an inner diameter 164 for the lower cavity 160. In the illustrated example external fixation stabilizer 100, the inner diameter 164 of the lower cavity 160 is less than the inner diameter 144 of the upper cavity 140. In this example, this configuration is considered advantageous at least because it provides a desirable interface between the connecting member 112 and the base member 110. It is noted, though, that other relative configurations of the upper 160 and lower 140 cavities can be included in an external fixation stabilizer according to a particular embodiment.

The connector member 112 has a base 170, a circumferential flange 171, and a shaft 172 extending away from the base 170. The base 170 has a base outer diameter 174 and the shaft 172 has a shaft outer diameter 176. The base outer diameter 174 is greater than the shaft outer diameter 176 and is greater than the opening inner diameter 136. The shaft outer diameter 176 is less than the base outer diameter 174 and is less than the opening inner diameter 136. As best illustrated in FIG. 4, this structural configuration positions the base 170 within the lower cavity 160 of the base member 110 and prevents its movement beyond the opening 134. Similarly, this structural configuration positions a portion of the shaft 172 within the opening 134, the circumferential flange 171 within the upper cavity 140 of the base member 110, and an extension portion 173 of the shaft 172 extending beyond the upper cavity 140 and the upper surface 120 of the base member 110.

In this example, base 170 defines a faceted outer surface 178 that facilitates interaction with tools that can used during securement of the external fixation stabilizer to another member, such as an external fixation frame. For example, in the illustrated example, the outer surface 178 defines a hexagon that can be received by standard sockets and wrenches. The base can define any suitable structure for interacting with any tool or tools that may be desired for use in securing a external fixation stabilizer to an external fixation frame, and a skilled artisan will be able to select an appropriate structure for the base in an external fixation stabilizer according to a particular embodiment based on various considerations, including the structure of any tool desired to be used to secure the external fixation stabilizer during to an external fixation frame. Examples of suitable structures for the base in example external fixation stabilizers include faceted outer surfaces of standard and non-standard configurations and sizes for interaction with sockets, wrenches, and/or other external grasping tools, and recesses on the terminal surface of the base that are suitable for receiving a portion of a driving tool, such as a screwdriver or other tool.

In this example, shaft 172 defines a continuous outer surface 180 that is substantially smooth and free of ribs, threads, or other structural interruptions to the surface 180. This structural configuration is considered advantageous at least because it provides options for securing the external fixation stabilizer 100 to an external fixation frame. For example, the shaft 172 can be modified to include a passageway that will accept a pin or other member to secure the external fixation stabilizer 100 to an external fixation frame. The shaft 172 and its outer surface 180 can define any suitable structure for securing a external fixation stabilizer to an external fixation frame, and a skilled artisan will be able to select an appropriate structure for the shaft and its outer surface in an external fixation stabilizer according to a particular embodiment based on various considerations, including the structure of any external fixation frame with which the external fixation stabilizer is desired to be used, whether it is desirable to discourage or prevent removal of the external fixation stabilizer from an external fixation frame after the external fixation stabilizer has been secured to an external fixation frame, and other considerations. Examples of suitable structures for the shaft in example external fixation stabilizers include a threaded outer surface, an outer surface that defines one or more detents, and an outer surface that defines one or more passageways, and other suitable structures.

An optional washer can be positioned between the base 170 of the connector member 112 and the base member 110, as an alternative to or in addition to circumferential flange 171.

The footing member 114 is disposed on the lower surface 122 of the base member 122 and, in the illustrated example, partially on the outer circumferential wall 124 of the base member 110. As such, the footing member 114 has a lower portion 184 that is disposed adjacent, and in contact with, the lower surface 122 of the base member 110 and an upper portion 186 that is disposed radially outward of, and in contact with, a portion of the outer circumferential wall 124 of the base member 110. As best illustrated in FIG. 3, the footing member 114 does not extend into the lower cavity 160 of the base member. This is considered advantageous at least because positioning of a portion of the footing member 114 in the lower cavity 160 may subject it to contact with a tool or tools used to secure the connector member 112 of the external fixation stabilizer to an external fixation frame, which could impact the structural integrity of the footing member 114. As described below, the footing member 114 is formed of a relatively soft material. As such, eliminating or reducing the possibility of unnecessary interaction with other components is desirable.

The lower portion 184 of the footing member 114 in the illustrated example includes a series of channels 188. While inclusion of the series of channels 188 is optional, its inclusion is considered advantageous at least because the series of channels 188 enhances gripping of a surface, such as a floor, by the footing member 114 when the external fixation stabilizer 100 is used with a footplate or other suitable external fixation frame. The lower portion of the footing member in an external fixation stabilizer can have any suitable structure and a skilled artisan will be able to select a suitable structure for a lower portion of the footing member in an external fixation stabilizer according to a particular embodiment based on various considerations, including any desired surface gripping properties. Examples of suitable structures include the series of channels 188 illustrated in FIGS. 1-4, one or more protuberances, one or more cavities, combinations of protuberances and cavities, and other suitable structures.

The upper portion 186 of the footing member 114 extends from the lower portion 184 along the outer circumferential wall 124 toward the upper surface 120. In the illustrated example, the upper portion 186 of the footing member 114 extends along only a portion of the axial length of the base member 110. In this example, the upper portion 186 of the footing member 114 extends along about half of the axial length of the base member 110. It is noted, though, that the upper portion of the footing member in an external fixation stabilizer according to a particular embodiment can extend along any suitable axial length of the base member of the external fixation stabilizer. Examples of suitable axial lengths of the base member for the upper portion of the footing member to extend include, but are not limited to, about entire axial length of the base member, the entire axial length of the base member, more than half of the axial length of the base member, about half of the axial length of the base member, half about the axial length of the base member, less than half of the axial length of the base member, about one-fourth of the axial length of the base member, and one-fourth of the axial length of the base member.

Figures 5, 6, 7:
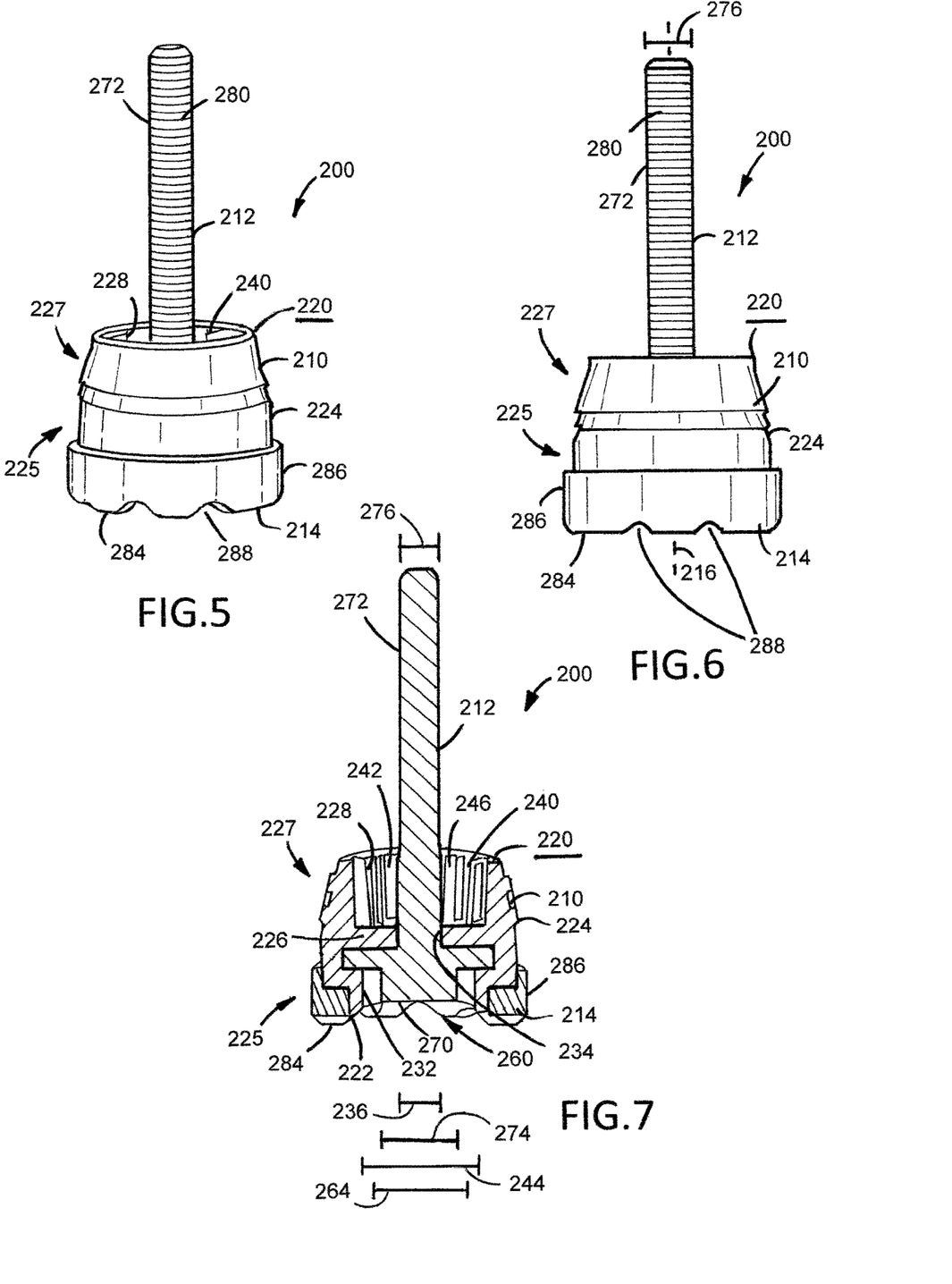
FIG. 5 is a perspective view of a second example external fixation stabilizer.
FIG. 6 is a side view of the second example external fixation stabilizer.
FIG. 7 is a sectional view of the second example external fixation stabilizer, taken along line 7-7 in FIG. 6.

FIGS. 5, 6, and 7 illustrate a second example external fixation stabilizer 200. The external fixation stabilizer 200 is similar to the external fixation stabilizer 100 described above and illustrated in FIGS. 1, 2, 3, and 4, except as detailed below. Thus, external fixation stabilizer 200 includes a base member 210, a connector member 212 extending away from the base member 210, and a footing member 214 secured to the base member 210. The external fixation stabilizer 200 and its base member 210, connector member 212, and footing member 214 share common lengthwise axis 216.

Base member 210 has an upper surface 220, a lower surface 222, an outer circumferential wall 224, a separating wall 226 that lies on a plane that is perpendicular to common lengthwise axis 216, and a circumferential shoulder 206 that lies on a plane that is perpendicular to common lengthwise axis 116. An upper inner circumferential wall 228 and the separating wall 226 cooperatively define an upper cavity 240 that extends from the upper surface 220, into the base member 210 to the separating wall 226. Similarly, a lower inner circumferential wall 232 and the separating wall 226 cooperatively define a lower cavity 260 that extends from the lower surface 222, into the base member 210 to the separating wall 226. Separating wall 226 defines an opening 234 having an opening inner diameter 236. The opening 234 provides communication between the upper cavity 240 and the lower cavity 260. As best illustrated in FIG. 7, the connector member 212 extends through the opening 234 such that a portion of the connector member 212 is disposed in the lower cavity 260, a portion of the connector member 212 is disposed in the upper cavity 240, and a portion of the connector member 212 is disposed in the opening 234 of the separating wall 226. The lower inner circumferential wall 232 is a continuous annular surface 262 free of corrugations or other structural interruptions to the surface 262. In this example, circumferential shoulder 206 and the separating wall 226 define a circumferential recess 207, which constitutes a portion of the lower cavity 260.

In this example, base member has a lower portion 225 the has a cylindrical configuration and an upper portion 227 that has a frustoconical configuration. As best illustrated in FIG. 7, the separating wall 226 is positioned such that the upper cavity 240 is positioned within the upper portion 227 of the base member 210 and such that the lower cavity 260 is positioned within the lower portion 225 of the base member 210.

The connector member 212 has a base 270, a circumferential flange 171, and a shaft 272 extending away from the base 270. The base 270 has a base outer diameter 274 and the shaft 272 has a shaft outer diameter 276. The base outer diameter 274 is greater than the shaft outer diameter 276 and is greater than the opening inner diameter 236. The shaft outer diameter 276 is less than the base outer diameter 274 and is less than the opening inner diameter 236. In this example, shaft 272 defines a threaded outer surface 280 onto which a nut or other threaded fastener can be attached to secure the external fixation stabilizer to an external fixation frame.

The footing member 214 is disposed on the lower surface 222 of the base member 222 and partially on the outer circumferential wall 224 of the base member 210. As such, the footing member 114 has a lower portion 284 that is disposed adjacent, and in contact with, the lower surface 222 of the base member 210 and an upper portion 286 that is disposed radially outward of, and in contact with, a portion of the outer circumferential wall 224 of the base member 110. The lower portion 284 of the footing member 214 in the illustrated example defines a series of channels 288. The upper portion 286 of the footing member 214 extends from the lower portion 284 along the outer circumferential wall 224 toward the upper surface 220. In this example, the upper portion 286 of the footing member 214 extends along only a portion of the axial length of the lower portion 225 of the of the base member 210.

The upper inner circumferential wall 228 defines a diameter 244 for the upper cavity 240 and the lower circumferential wall 232 defines a diameter 264 for the lower cavity 260. In this example, the diameter 264 of the lower cavity 260 is less than the diameter 244 of the upper cavity 240. In this example, this configuration is considered advantageous at least because it allows larger items to enter the upper cavity 240 than the lower cavity 240, such as the spacers described below.

As best illustrated in FIGS. 5 and 7, the upper inner circumferential wall 228 is a corrugated annular surface 242 that defines a plurality of ribs 246 that, together, define an interrupted frustoconical surface 244 within the upper cavity 240. In the illustrated example each rib 248 of the plurality of ribs 246 extends at an angle to the common lengthwise axis 216 from the upper surface 220 to the separating wall 226.

Figure 8:
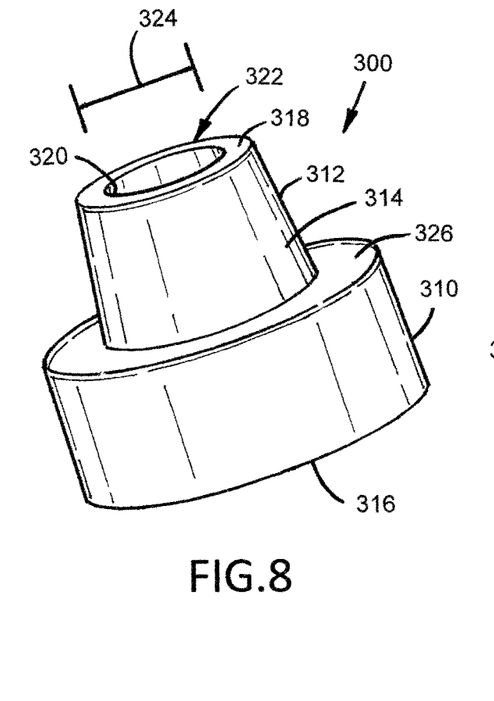
FIG. 8 is a perspective view of an example spacer for use with an external fixation stabilizer.
Figure 9:
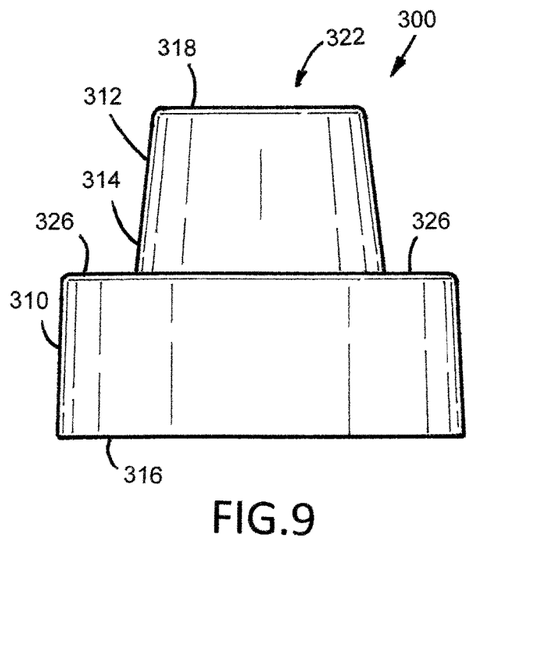
FIG. 9 is a side view of the example spacer illustrated in FIG. 8.
Figure 10:
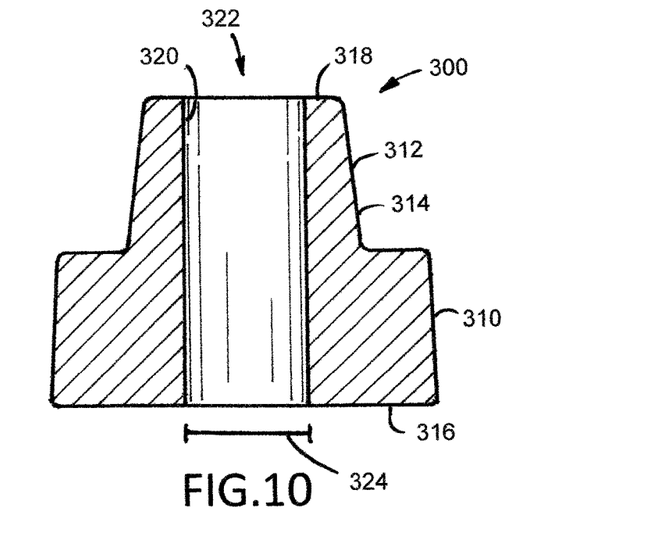
FIG. 10 is a sectional view of the example spacer illustrated in FIG. 8, taken along line 10-10 in FIG. 9.

FIGS. 8, 9, and 10 illustrate an example spacer 300 for use with an external fixation stabilizer, such as external fixation stabilizer 100 and external fixation stabilizer 200. Spacer 300 has a base portion 310, an extension portion 312, and an outer wall 314. The base portion 310 defines a first terminal surface 316 and the extension portion 312 defines a second terminal surface 318. An inner circumferential wall 320 defines a passageway 322 that extends from the first terminal surface 316 to the second terminal surface 318. Thus, the passageway 322 extends through the entire axial length of the spacer 300, through both the base portion 310 and the extension portion 312. The passageway 322 has an inner diameter 324 that is advantageously constant over the axial length of the passageway 322.

As best illustrated in FIGS. 8 and 9, outer wall 314 defines shoulder 326 that forms the interface between the base portion 310 and the extension portion 312. Also as best illustrated in FIG. 9, each of the base portion 310 and the extension portion 312, in this example, has a frustoconical configuration, with the base portion 310 having a smaller difference between its larger diameter and its smaller diameter than the difference between the larger diameter and smaller diameter of the extension portion 312.

In the example spacer 300, the inner circumferential wall 320 is a continuous annular surface 330 free of ribs or other structural interruptions to the surface 330. This configuration is considered advantageous at least because it allows the spacer 300 to be used with a variety of external fixation stabilizers, regardless of the structure defined by the external surface of the shaft of the connector member of the external fixation stabilizer. For example, the illustrated spacer 300 can be used with an external fixation stabilizer having a connector member with a shaft that defines a continuous outer surface, such as the external fixation stabilizer 100 described above and illustrated in FIGS. 1, 2, 3, and 4. Also, the illustrated spacer 300 can be used with an external fixation stabilizer having a connector member with a shaft that defines a threaded outer surface, such as the external fixation stabilizer 200 described above and illustrated in FIGS. 5, 6, and 7. The passageway 322 need only have an outer diameter 324 that permits the spacer 300 to be passed over the shaft of the selected external fixation stabilizer.

Alternatively, the inner circumferential wall of a spacer according to a particular embodiment can define a tapering diameter or structural features that facilitate securement of the spacer to an object, such as the shaft of an external fixation stabilizer. For example, the inner circumferential wall of a spacer according to a particular embodiment can define a threaded surface for mating with a threaded outer surface of a shaft of a connector member in a particular external fixation stabilizer.

Figure 11:
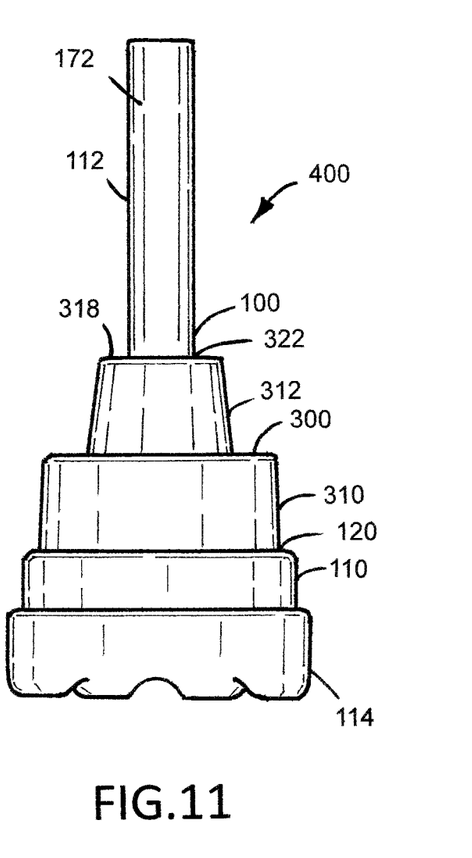
FIG. 11 is a side view of a first example external fixation stabilizer assembly including the example external fixation stabilizer illustrated in FIG. 1 and the example spacer illustrated in FIG. 8.
Figure 12:
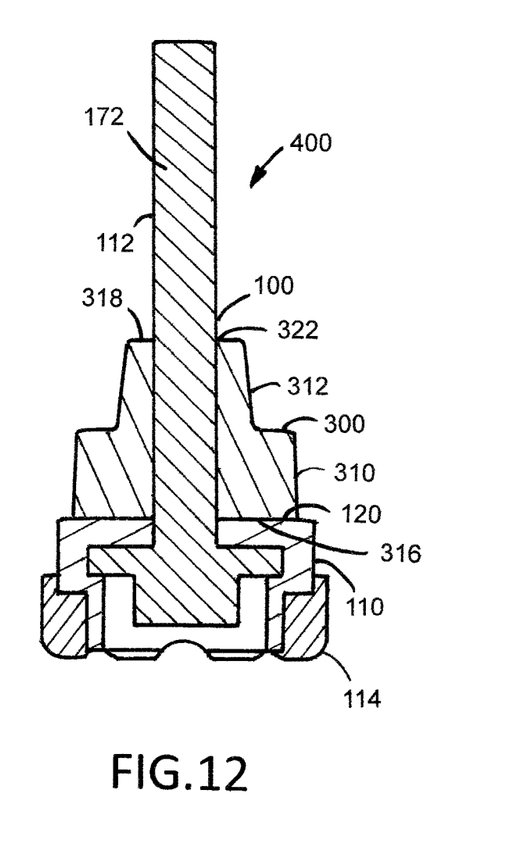
FIG. 12 is a sectional view of the first example external fixation stabilizer assembly, taken along line 12-12 in FIG. 11.

FIGS. 11 and 12 illustrate a first example external fixation stabilizer assembly 400. In this example, the external fixation stabilizer assembly 400 includes external fixation stabilizer 100 and spacer 300. The shaft 172 of the connector member 112 of the external fixation stabilizer 100 extends through the passageway 322 of the spacer 300. The first terminal surface 316 of the base portion 310 of the spacer 300 is disposed adjacent, and in contact with, the upper surface 120 of the base member 110 of the external fixation stabilizer 100. The second terminal surface 318 of the base portion 310 of the spacer 300 is disposed away from, and free of contact with, the upper surface 120 of the base member 110 of the external fixation stabilizer 100. As such, the spacer 300 is positioned on the connector member 112 with the base portion 310 disposed adjacent, and in contact with, the upper surface 120 of the base member 110 of the external fixation stabilizer 100. The extension portion 312 is disposed away from, and not in contact with, the upper surface 120 of the base member 110 of the external fixation stabilizer 100.

Figure 13:
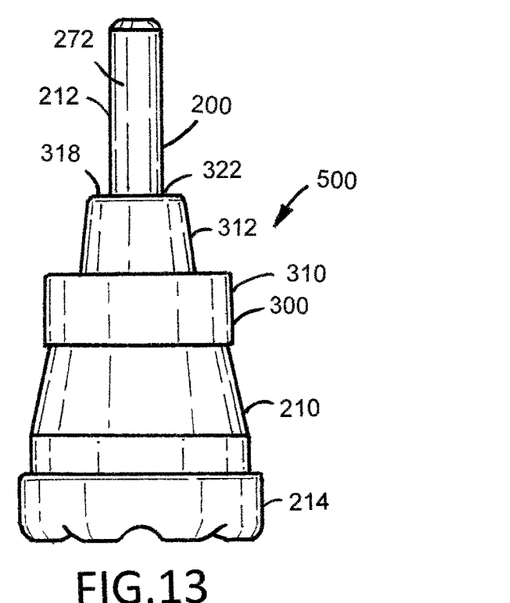
FIG. 13 is a side view of a second example external fixation stabilizer assembly including the example external fixation stabilizer illustrated in FIG. 5 and the example spacer illustrated in FIG. 8. The example spacer is illustrated in a first orientation.
Figure 14:
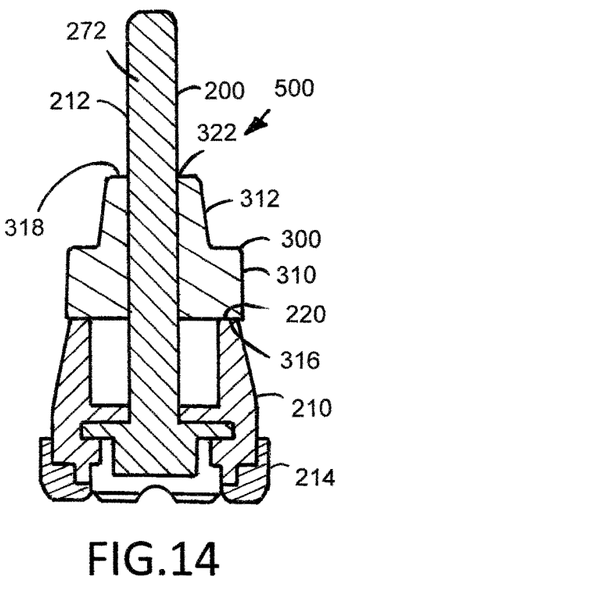
FIG. 14 is a sectional view of the second example external fixation stabilizer assembly, taken along line 14-14 in FIG. 13.

FIGS. 13 and 14 illustrate a second example external fixation stabilizer assembly 500. In this example, the external fixation stabilizer assembly 500 includes external fixation stabilizer 200 and spacer 300. The spacer 300 is positioned on the external fixation stabilizer 200 in a first orientation with the base portion 310 disposed adjacent, and in contact with, the upper surface 220 of the base member 210 of the external fixation stabilizer 200 and the extension portion 312 disposed away from, and not in contact with, the upper surface 220 of the base member 210 of the external fixation stabilizer 200.

The shaft 272 of the connector member 212 of the external fixation stabilizer 200 extends through the passageway 322 of the spacer 300. The first terminal surface 316 of the base portion 310 of the spacer 300 is disposed adjacent, and in contact with, the upper surface 220 of the base member 210 of the external fixation stabilizer 200. The second terminal surface 318 of the base portion 310 of the spacer 300 is disposed away from, and free of contact with, the upper surface 220 of the base member 210 of the external fixation stabilizer 200. As such, the spacer 300 is positioned on the connector member 212 with the base portion 310 disposed adjacent, and in contact with, the upper surface 220 of the base member 210 of the external fixation stabilizer 200. The extension portion 312 is disposed away from, and not in contact with, the upper surface 220 of the base member 210 of the external fixation stabilizer 200.

Figure 15:
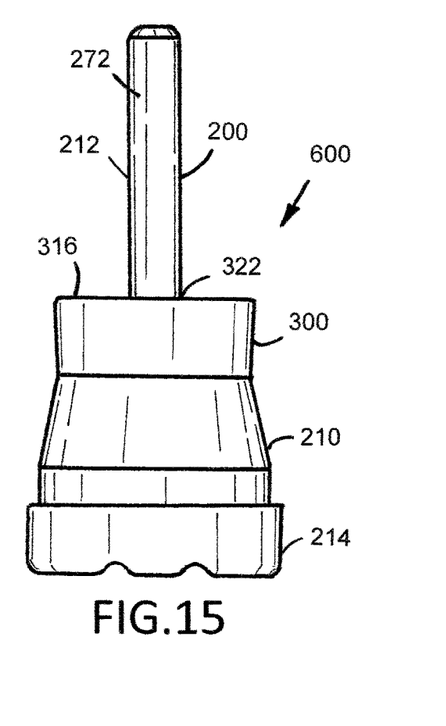
FIG. 15 is a side view of a third example external fixation stabilizer assembly including the example external fixation stabilizer illustrated in FIG. 5 and the example spacer illustrated in FIG. 8. The example spacer is illustrated in a second orientation.
Figure 16:
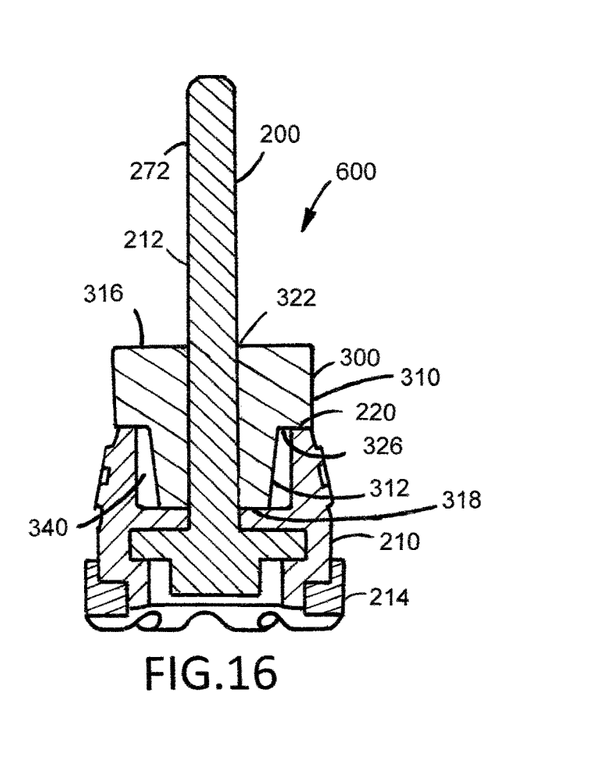
FIG. 16 is a sectional view of the third example external fixation stabilizer assembly, taken along line 16-16 in FIG. 15.

FIGS. 15 and 16 illustrate a third example external fixation stabilizer assembly 600. Similar to external fixation stabilizer assembly 500 described above and illustrated in FIGS. 13 and 14, external fixation stabilizer assembly 600 includes external fixation stabilizer 200 and spacer 300. In this example, though, the spacer 300 is positioned on the external fixation stabilizer 200 in a second orientation with the extension portion 310 disposed in the upper cavity 340 defined by the base member 210 of the external fixation stabilizer 200 such that the shoulder 326 of the spacer 300 is disposed adjacent, and in contact with, the upper surface 220 of the base member 210 of the external fixation stabilizer 200.

The shaft 272 of the connector member 212 of the external fixation stabilizer 200 extends through the passageway 322 of the spacer 300. The second terminal surface 318 of the extension portion 312 of the spacer 300 is disposed adjacent, and in contact with, the separating wall 226 of the base member 210 of the external fixation stabilizer 200. The first terminal surface 316 of the base portion 310 of the spacer 300 is disposed away from, and free of contact with, the upper surface 220 of the base member 210 of the external fixation stabilizer 200. As such, the spacer 300 is positioned on the connector member 212 with the extension portion 310 disposed substantially within the upper cavity 240 of the base member 210 of the external fixation stabilizer 200. The base portion 310 is disposed such that the shoulder 326 is in contact with the upper surface 220 of the base member 210 of the external fixation stabilizer 200.

Figure 17:
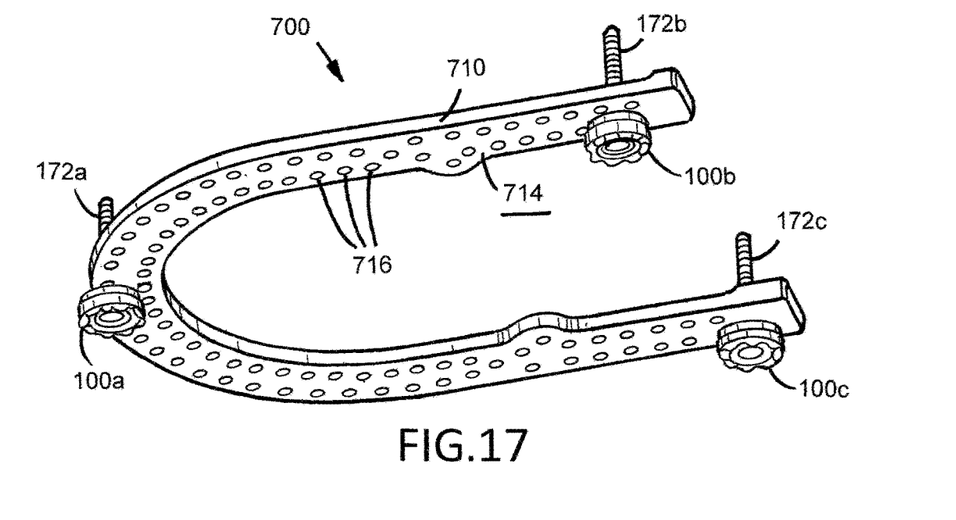
FIG. 17 is a perspective view of a first example external fixation system.
Figure 18:
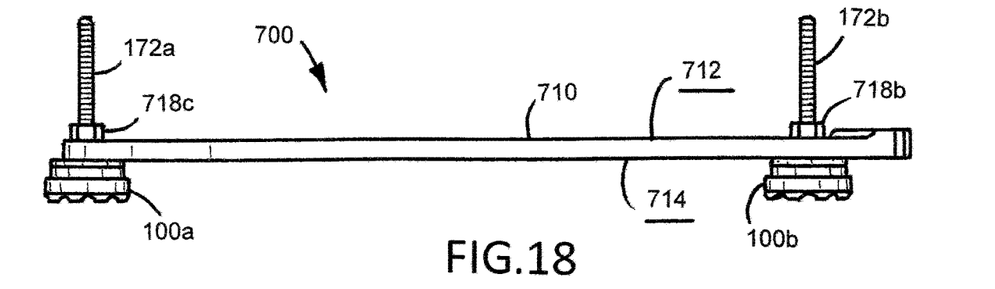
FIG. 18 is a side view of the first example external fixation system.

FIGS. 17 and 18 illustrate a first example external fixation system 700. In this example, the external fixation system 700 includes external fixation plate 710 and three external fixation stabilizers 100a, 100b, and 100c, each of which is an alternative of the external fixation stabilizer 100 described above and illustrated in FIGS. 1, 2, 3, and 4. The external fixation plate 710 is a u-shaped member having upper 712 and lower 714 surfaces. The external fixation plate 710 is suitable for use as a footplate for external fixation. The external fixation plate 710 defines a plurality of passageways 716. Each passageway of the plurality of passageways 716 extends through the entire thickness of the external fixation plate, from the upper surface 712 to the lower surface 714. Also, each passageway of the plurality of passageways 716 has an inner diameter that is larger than the outer diameter of the shaft 172 of a connector member 112 of at least one of the external fixation stabilizers 100a, 100b, 100c such that one of the external fixation stabilizers 100a, 100b, 100c can be positioned with the shaft 172 extending through the passageway of the plurality of passageways 716. In the illustrated embodiment, each of the external fixation stabilizers 100a, 100b, 100c includes shaft 172 of the same outer diameter and each passageway of the plurality of passageways has the same inner diameter. This configuration is considered advantageous at least because it maximizes the possible connections between the external fixation stabilizers 100a, 100b, and 100c and the external fixation plate 710. It is noted, though, that an external fixation system according to a particular embodiment can include external fixation stabilizers having shafts of different diameters and/or an external fixation plate with passageways of different inner diameters. In this example, the shaft 172a, 172b, 172c of each of the external fixation stabilizers 100a, 100b, and 100c includes a threaded outer surface 180a, 180b, 180c. As best illustrated in FIG. 18, a nut 718a, 718b, 718c is included for each of the external fixation stabilizers 100a, 100b, and 100c and is secured to the threaded outer surface of the shaft 172a, 172b, 172c of the respective external fixation stabilizer 100a, 100b, and 100c such that a portion of the external fixation plate 710 is clamped between the nut and the upper surface 120a, 120b, 120c of the respective external fixation stabilizer 100a, 100b, and 100c.

External fixation system 700 can include one or more additional components, including conventional external fixation components, including, but not limited to, foot plates, rings, connecting elements such as rods, struts and bone fixation wires.

Figure 19:
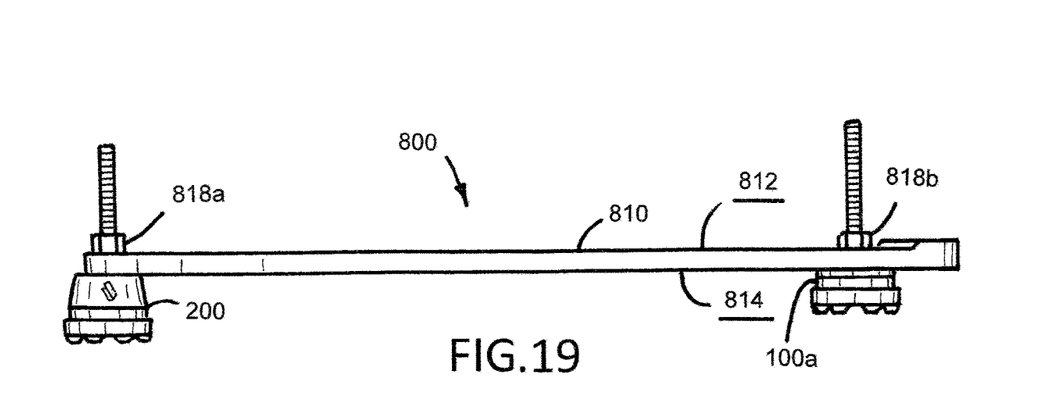
FIG. 19 is a side view of a second example external fixation system.

FIG. 19 illustrates a second example external fixation system 800. In this example, the external fixation system 800 includes external fixation plate 810 and two external fixation stabilizers 100a, 100b (not visible in FIG. 19), each of which is a an alternative of the external fixation stabilizer 100 described above and illustrated in FIGS. 1, 2, 3, and 4, and one external fixation stabilizer 200 that is the external fixation stabilizer 200 described above and illustrated in FIGS. 5, 6, and 7. The external fixation plate 810 is a u-shaped member having upper 812 and lower 814 surfaces. The external fixation plate 810 is suitable for use as a footplate for external fixation. The external fixation plate 810 defines a plurality of passageways 816. Each passageway of the plurality of passageways 816 extends through the entire thickness of the external fixation plate, from the upper surface 812 to the lower surface 814. Also, each passageway of the plurality of passageways 816 has an inner diameter that is larger than the outer diameter of the shaft of a connector member of at least one of the external fixation stabilizers 100a, 100b, 200a such that one of the external fixation stabilizers 100a, 100b, 200 can be positioned with the shaft 172 extending through the passageway of the plurality of passageways 816. Inclusion of different types of external fixation stabilizers 100a, 100b, 200 is considered advantageous at least because the different types of external fixation stabilizers can be arranged in various configurations relative to the external fixation plate to provide different angles for the external fixation plate 810 relative to the earth or a floor, which can be desirable in external fixation of foot and ankle bones. This enables a caregiver to arrange the external fixation system in a manner the specifically accommodates the needs of a particular patient which may arise due to various factors, such as individual anatomy and the location and/or spatial positioning of a previously placed implant, such as an implanted foot plate, for example.

External fixation system 800 can include one or more additional components, including conventional external fixation components, including, but not limited to, foot plates, rings, connecting elements such as rods, struts and bone fixation wires.

The modular nature of the external fixation systems, such as external fixation system 700 and external fixation system 800, is considered advantageous at least because it allows a caregiver to easily remove an external fixation stabilizer from an external fixation plate when it shows signs of wear. This provides significant advantage in the correction of deformities. For example, in the correction of a foot and/or ankle deformity, a caregiver can easily remove and replace external fixation stabilizers as a new ground contact plane is desired.

Figure 20:
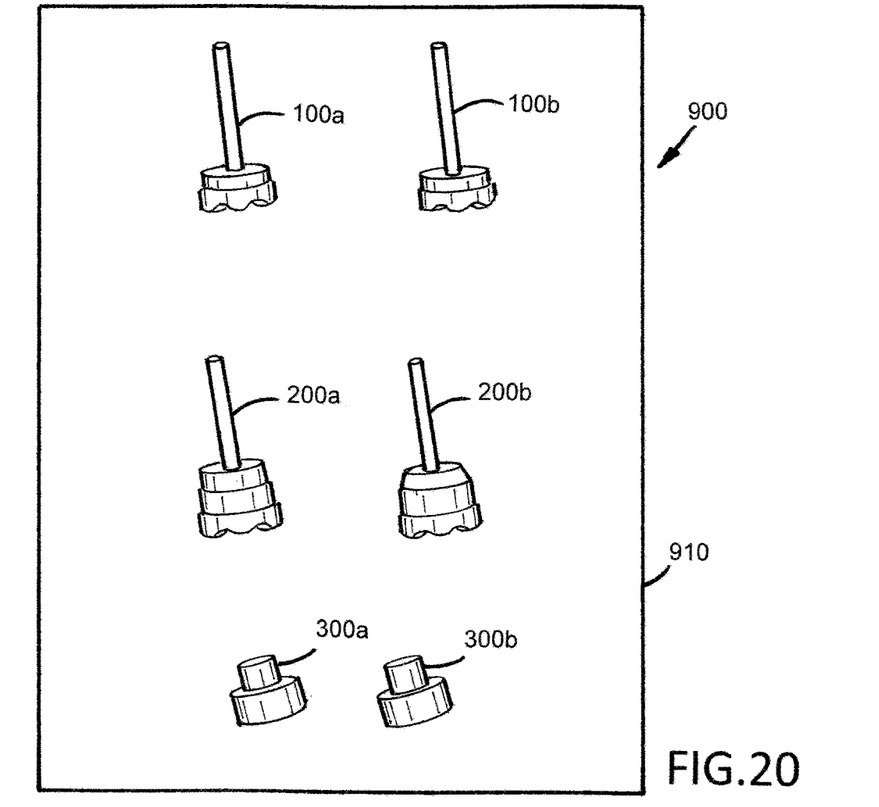
FIG. 20 is a schematic illustration of a first example external fixation kit.

FIG. 20 illustrates a first example external fixation kit 900. The kit 900 includes external fixation stabilizers 100a, 100b, 200a, 200b, spacers 300a, 300b, and packaging substrate 910. In the illustrated example, each of external fixation stabilizers 100a, 100b represents the external fixation stabilizer 100 described above and illustrated in FIGS. 1, 2, 3, and 4. Each of external fixation stabilizers 200a, 200b represents the external fixation stabilizer 200 described above and illustrated in FIGS. 5, 6, and 7. Each of spacers 300a, 300b represents the spacer 300 described above and illustrated in FIGS. 8 and 9. Optional components for the kit include written instructions for use or other printed matter.

Any suitable number, types, and relative numbers of different types of external fixation stabilizers can be included in an external fixation kit according to a particular embodiment and the total number, types, and relative numbers of different types of external fixation stabilizers 100a, 100b, 200a, 200b illustrated in FIG. 20 are for example only. A skilled artisan will be able to select an appropriate total number, types, and relative numbers of different types of external fixation stabilizers for inclusion in a kit according to a particular embodiment based on various considerations, including the nature of a bone or bones with which the external fixation kit is intended to be used. Furthermore, any suitable number of spacers can be included in an external fixation kit according to a particular embodiment. Examples of suitable numbers of spacers for inclusion in an external fixation kit include, but are not limited to, a number that is greater than the total number of external fixation stabilizers included in the external fixation kit, a number that is equal to the total number of external fixation stabilizers included in the external fixation kit, and a number that is less than the total number of external fixation stabilizers included in the external fixation kit.

Packaging substrate 910 can comprise any substrate considered suitable for packaging a kit that contains medical device components. Examples of suitable packaging substrates include a box or other member that defines a cavity into which some or all of the components of the kit can be placed. The box or other member can include one or more parts, such as a cavity defining portion and a movable flap that provides access to the cavity. Alternatively, the body portion can define a cavity and a separable lid portion can be provided as part of the packaging substrate. Alternatively, the packaging substrate can simply define a surface onto which the components of the kit can be placed and secured, such as a backing and a shrink wrap element.

Figure 21:
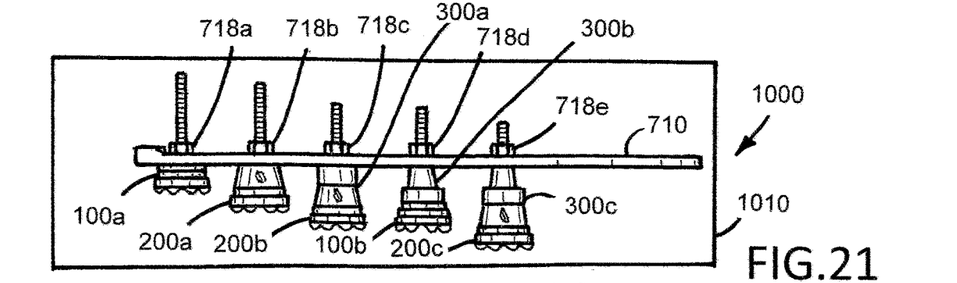
FIG. 21 is a schematic illustration of a second example external fixation kit.

FIG. 21 illustrates a second example external fixation kit 1000. The kit 1000 includes external fixation stabilizers 100a, 100b, 200a, 200b, 200c, spacers 300a, 300b, 300c, external fixation plate 710, and packaging substrate 1010. A nut 718a, 718b, 718c, 718d, 718e is included for each of the external fixation stabilizers 100a, 100b, 200a, 200b, 200c and is adapted to be secured to the threaded outer surface of the shaft 172a, 172b, 172c, 172d, 172e of at least one of the external fixation stabilizers 100a, 100b, 200a, 200b, 200c. In the illustrated example, each of external fixation stabilizers 100a, 100b represents and alternative of the external fixation stabilizer 100 described above and illustrated in FIGS. 1, 2, 3, and 4. Each of external fixation stabilizers 200a, 200b, 200c represents the external fixation stabilizer 200 described above and illustrated in FIGS. 5, 6, and 7. Each of spacers 300a, 300b, 300c represents the spacer 300 described above and illustrated in FIGS. 8 and 9. External fixation plate 710 represents the external fixation plate described above and illustrated in FIGS. 17 and 18. Optional components for the kit include written instructions for use or other printed matter.

Figure 22:
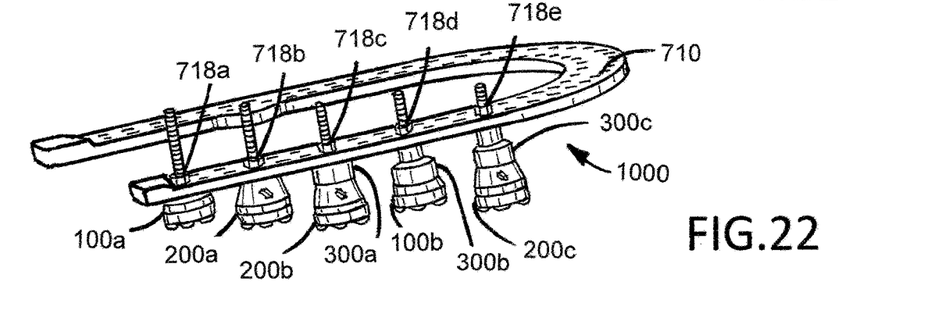
FIG. 22 is a perspective view of the external fixation plate and attached external fixation stabilizers and spacers of the external fixation kit illustrated in FIG. 21.

FIG. 22 illustrates a perspective view of the external fixation plate 710 with attached external fixation stabilizers 100a, 100b, 200a, 200b, 200c, spacers 300a, 300b, 300c, and nuts 718a, 718b, 718c, 718d, 718e. This view illustrates the variety of arrangements that can be achieved by varying the assembly of external fixation stabilizers with and without spacers, as described herein. For illustration purposes, all external fixation stabilizers 100a, 100b, 200a, 200b, 200c are shown attached to the same side of external fixation plate 710. It is noted that, in use, one or more external fixation stabilizers will typically be attached to each side of the external fixation plate 710, and perhaps the segment that connects the sides of the plate 710. Use in the illustrated configuration is, however, certainly possible.

The components of the various external fixation stabilizers according to all embodiments can be made of any suitable material. The inventors have determined that it is advantageous to fabricate the base member of an external fixation stabilizer out of a relatively hard plastic material. Examples of suitable materials for the base member include, but are not limited to, polyamide, polycarbonate, acrylonitrile butadiene styrene (ABS), ABS polycarbonate blends, polyether ether ketone (PEEK), polypropylene, and polyurethane. Also, the inventors have determined that is advantageous to fabricate the footing member of an external fixation stabilizer out of a relatively soft material. Examples of suitable materials for the footing member include, but are not limited to, polypropylene, high density polyethylene, a thermoplastic elastomer (TPE), bromobutyl, chlorobutyl, polyurethane, polyvinyl chloride, and rubber. The inventors have determined that the base member and footing member can be advantageously fabricated using a two-shot overmold process.

Also, the inventors have determined that it is advantageous to fabricate the spacer out of a resilient plastic material at least because such materials absorb a portion of a mechanical load applied to the spacer during use, such as when a patient is walking with an external fixation system applied to his or her foot. Examples of suitable materials for the footing member include, but are not limited to, polypropylene, high density polyethylene, and rubber. Also, the inventors have determined that it is advantageous to fabricate the connector member of an external fixation stabilizer out of a metal, such as stainless steel, aluminum, titanium, zinc, or other suitable metal. Also, the inventors have determined that is advantageous to fabricate the external fixation plates out of a metal, such as stainless steel, aluminum, titanium, zinc, or other suitable metal.

FIG. 22 illustrates a flowchart representation of an example method 2000. A step 2002 comprises attaching a first external fixation stabilizer according to an embodiment to an external fixation plate. Another step 2004 comprises attaching a second external fixation stabilizer according to an embodiment to the external fixation plate.

In the method 2000, any suitable external fixation stabilizer according to an embodiment can be used, including the external fixation stabilizer 100 described above and illustrated in FIGS. 1, 2, 3, and 4, and the external fixation stabilizer 200 described above and illustrated in FIGS. 5, 6, and 7.

An optional step 2006 comprises attaching another external fixation stabilizer according to an embodiment to the external fixation plate. This step 2006 can be repeated any desirable number of times.

Figure 23:
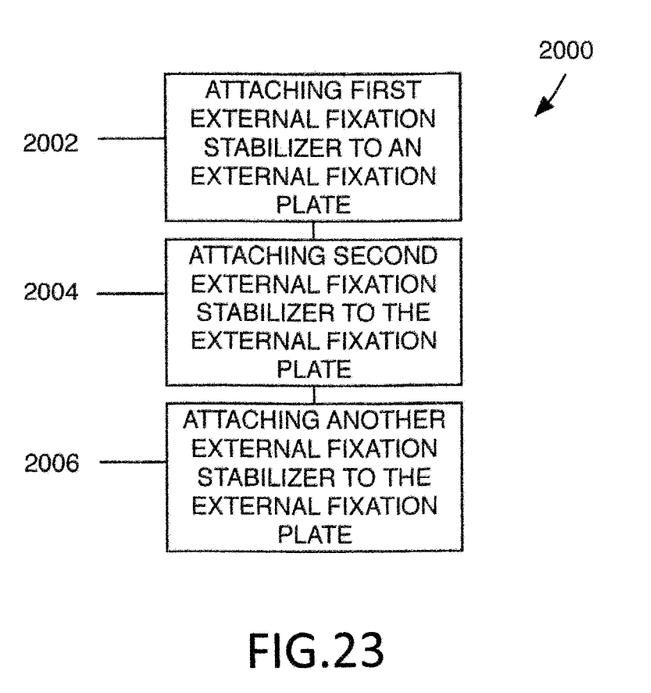
FIG. 23 is a flowchart representation of a first example method.
Figure 24:
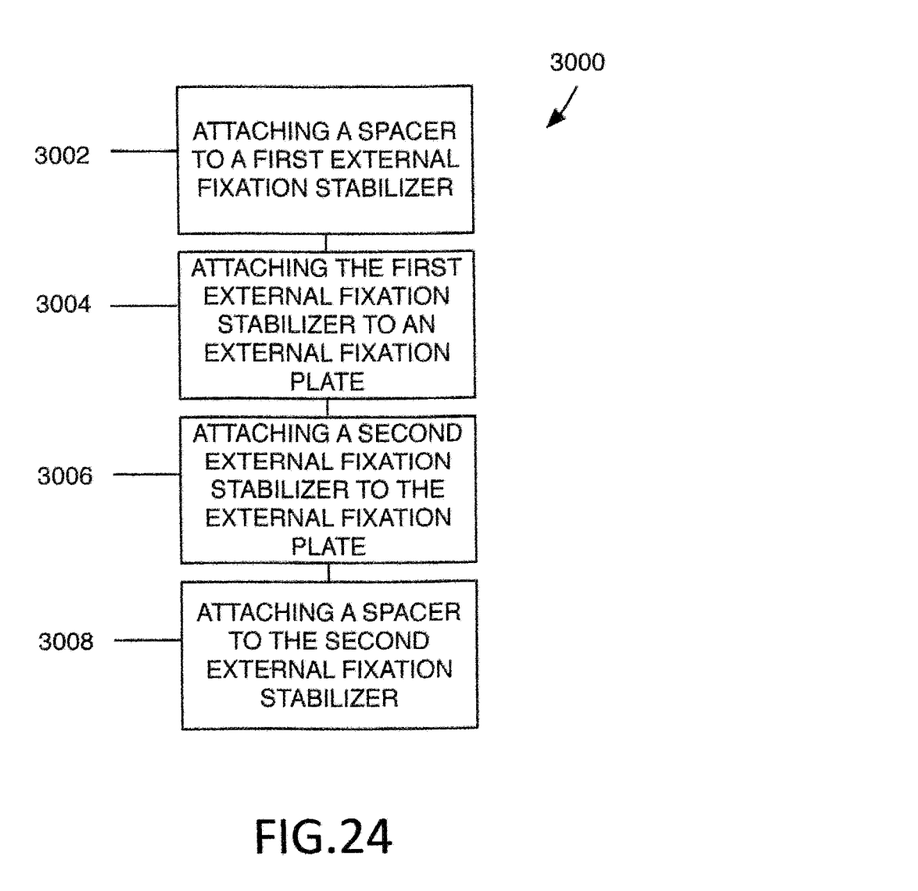
FIG. 24 is a flowchart representation of a second example method.

FIG. 23 illustrates a flowchart representation of an example method 3000. A step 3002 comprises attaching a spacer to a first external fixation stabilizer according to an embodiment. Another step 3004 comprises attaching the first external fixation stabilizer to an external fixation plate. Another step 3006 comprises attaching a second external fixation stabilizer to the external fixation plate.

In the method 3000, any suitable external fixation stabilizer according to an embodiment can be used, including the external fixation stabilizer 100 described above and illustrated in FIGS. 1, 2, 3, and 4, and the external fixation stabilizer 200 described above and illustrated in FIGS. 5, 6, and 7. Also, any suitable spacer according to an embodiment can be used, including spacer 300 described above and illustrated in FIGS. 8 and 9.

An optional step 3008 comprises attaching a spacer to the second external fixation stabilizer. This step 3008, if included, should be performed before step 3006.

Any suitable number of additional optional steps of attaching another external fixation stabilizer to the external fixation plate can be included if desired. Also, for each additional step of attaching another external fixation stabilizer to the external fixation plate included in a particular method, an optional step of attaching a spacer to the external fixation stabilizer can be included and should be performed before the particular step of attaching another external fixation stabilizer to the external fixation plate.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular examples disclosed herein have been selected by the inventors simply to describe and illustrate examples of the invention and are not intended to limit the scope of the invention or its protection, which is to be given the full breadth of the appended claims and any and all equivalents thereof.

We claim:

1. An external fixation stabilizer assembly, comprising:
  a base member having an upper surface, a lower surface, an outer circumferential wall, an upper inner circumferential wall, a lower inner circumferential wall, and a separating wall defining an opening disposed between the upper inner circumferential wall and the lower inner circumferential wall, the upper inner circumferential wall and the separating wall cooperatively defining an upper cavity that extends from the upper surface to the separating wall, the upper cavity having an inner diameter, the lower inner circumferential wall and the separating wall cooperatively defining a lower cavity that extends from the lower surface to the separating wall;

a spacer having a base portion defining a first terminal surface and a first outer diameter that is greater than the inner diameter of the upper cavity, an extension portion defining a second terminal surface and a second outer diameter that is smaller than the inner diameter of the upper cavity, an outer wall defining a shoulder comprising an interface between the base portion and the extension portion, and an inner circumferential wall defining a passageway extending from the first terminal surface to the second terminal surface;

a connector member partially disposed in the lower cavity and having a shaft extending through the opening, and into the upper cavity and the passageway of the spacer; and a footing member attached to the lower surface of the base member.

2. The external fixation stabilizer assembly of claim 1, wherein the spacer is movable along the connector.

3. The external fixation stabilizer assembly of claim 1, wherein the spacer is movable between first and second orientations on the connector;
   wherein in the first orientation the extension portion of the spacer extends into the upper cavity of the base member; and
   wherein in the second orientation the extension portion of the spacer extends away from the upper cavity of the base member.

4. The external fixation stabilizer assembly of claim 1, wherein the footing member is disposed on the lower surface of the base member and partially on the outer circumferential wall of the base member.

5. The external fixation stabilizer assembly of claim 4, wherein the footing member has a lower portion that is disposed adjacent, and in contact with, the lower surface of the base member and an upper portion that is disposed radially outward of, and in contact with, the outer circumferential wall of the base member.

6. The external fixation stabilizer assembly of claim 5, wherein the lower portion of the footing member defines a series of channels.

7. The external fixation stabilizer assembly of claim 1, wherein the base member is non-metallic.

8. The external fixation stabilizer assembly of claim 7, wherein the footing member is non-metallic.

9. The external fixation stabilizer assembly of claim 8, wherein the base member is formed of a first material and the footing member is formed of a second, different material.

10. The external fixation stabilizer assembly of claim 9, wherein the first material is relatively harder than the second material.

11. The external fixation stabilizer assembly of claim 10, wherein the first material is selected from the group consisting of polyamide, polycarbonate, acrylonitrile butadiene styrene (ABS), an ABS polycarbonate blend, polyether ether ketone (PEEK), polypropylene, and polyurethane.

12. The external fixation stabilizer assembly of claim 11, wherein the second material is selected from the group consisting of polypropylene, high density polyethylene, a thermoplastic elastomer (TPE), bromobutyl, chlorobutyl, polyurethane, polyvinyl chloride, and rubber.

13. The external fixation stabilizer assembly of claim 9, wherein the connector member comprises a metal.

14. An external fixation stabilizer assembly, comprising:
    a base member having an upper surface, a lower surface, an outer circumferential wall, an upper inner circumferential wall, a lower inner circumferential wall, and a separating wall defining an opening disposed between the upper inner circumferential wall and the lower inner circumferential wall, the upper inner circumferential wall and the separating wall cooperatively defining an upper cavity that extends from the upper surface to the separating wall, the upper cavity having an inner diameter, the lower inner circumferential wall and the separating wall cooperatively defining a lower cavity that extends from the lower surface to the separating wall;

a spacer having a base portion defining a first terminal surface and a first outer diameter that is greater than the inner diameter of the upper cavity, an extension portion defining a second terminal surface and a second outer diameter that is smaller than the inner diameter of the upper cavity, an outer wall defining a shoulder comprising an interface between the base portion and the extension portion, and an inner circumferential wall defining a passageway extending from the first terminal surface to the second terminal surface, the spacer movable between a first orientation on the connector in which the extension portion extends into the upper cavity of the base member and a second orientation on the connector in which the extension portion extends away from the upper cavity of the base member;

a connector member partially disposed in the lower cavity and having a shaft extending through the opening, and into the upper cavity and the passageway of the spacer; and a footing member disposed on the lower surface of the base member and extending along a portion of the outer circumferential wall of the base member.

15. The external fixation stabilizer assembly of claim 14, wherein the base member is formed of a first material and the footing member is formed of a second, different material.

16. The external fixation stabilizer assembly of claim 15, wherein the first material is relatively harder than the second material.

17. The external fixation stabilizer assembly of claim 16, wherein the connector member comprises a metal.

18. An external fixation system, comprising:
    a plate having a plate upper surface and a plate lower surface and defining a first plate passageway extending from the plate lower surface to the plate upper surface, a second plate passageway extending from the plate lower surface to the plate upper surface, and a third plate passageway extending from the plate lower surface to the plate upper surface;

a first external fixation stabilizer comprising a first base member having a first upper surface and a first lower surface, a first connector member extending away from the first upper surface of the first base member and through the first plate passageway, and a first footing member attached to the first lower surface of the first base member;

a second external fixation stabilizer comprising a second base member having a second upper surface and a second lower surface, a second connector member extending away from the second upper surface of the second base member and through the second plate passageway, and a second footing member attached to the second lower surface of the second base member;

a third external fixation stabilizer comprising a third base member having a third upper surface and a third lower surface, a third connector member extending away from the third upper surface of the third base member and through the third plate passageway, and a third footing member attached to the third lower surface of the third base member; and a first spacer having a first spacer base portion defining a first spacer first terminal surface and a first outer diameter, a first spacer extension portion defining a first spacer second terminal surface and a second outer diameter that is less than the first outer diameter, a first spacer outer wall defining a first spacer shoulder comprising a first spacer interface between the first spacer base portion and the first spacer extension portion, and a first spacer inner circumferential wall defining a first spacer passageway extending from the first spacer first terminal surface to the first spacer second terminal surface, the first spacer movable between a first spacer first orientation on the first connector in which the first spacer extension portion extends toward the upper surface of the first base member and a first spacer second orientation on the first connector in which the first spacer extension portion extends away from the upper surface of the first base member.

19. The external fixation system of claim 18, further comprising a second spacer having a second spacer base portion defining a second spacer first terminal surface, a second spacer extension portion defining a second spacer second terminal surface, a second spacer outer wall defining a second spacer shoulder comprising a second spacer interface between the second spacer base portion and the second spacer extension portion, and a second spacer inner circumferential wall defining a second spacer passageway extending from the second spacer first terminal surface to the second spacer second terminal surface, the second spacer movable between a second spacer first orientation on the second connector in which the second spacer extension portion extends toward the upper surface of the second base member and a second spacer second orientation on the second connector in which the second spacer extension portion extends away from the upper surface of the second base member.

20. The external fixation system of claim 19, in which the first spacer is disposed on the first connector member in the first spacer first orientation and the second spacer is disposed on the second connector member in the second spacer second orientation.

* * * * *